(12) United States Patent
Ratnam et al.

(10) Patent No.: US 7,951,937 B2
(45) Date of Patent: May 31, 2011

(54) PROCESS FOR PURIFICATION OF TRICHLOROGALACTOSUCROSE BASED ON DIRECT EXTRACTION IN ORGANIC SOLVENT FROM REACTION MIXTURE FOLLOWED BY EVAPORATIVE REMOVAL OF SOLVENT

(75) Inventors: Rakesh Ratnam, Bangalore (IN); Sundeep Aurora, Bangalore (IN); Batchu Chandrasekhar, Bangalore (IN)

(73) Assignee: V.B. Medicare Private Limited, Bangalore (IN)

( * ) Notice: Subject to any disclaimer, the term of this patent is extended or adjusted under 35 U.S.C. 154(b) by 510 days.

(21) Appl. No.: 11/991,144

(22) PCT Filed: Aug. 29, 2006

(86) PCT No.: PCT/IN2006/000328
§ 371 (c)(1),
(2), (4) Date: Apr. 16, 2008

(87) PCT Pub. No.: WO2007/052304
PCT Pub. Date: May 10, 2007

(65) Prior Publication Data
US 2009/0118493 A1      May 7, 2009

(30) Foreign Application Priority Data
Aug. 30, 2005 (IN) .......................... 1047/MUM/2005

(51) Int. Cl.
*C07H 1/06* (2006.01)
*C07H 1/08* (2006.01)

(52) U.S. Cl. ...................................................... 536/127
(58) Field of Classification Search .................. None
See application file for complete search history.

(56) References Cited

U.S. PATENT DOCUMENTS

| | | | | |
|---|---|---|---|---|
| 5,498,709 A | * | 3/1996 | Navia et al. .................. 536/124 |
| 5,530,106 A | * | 6/1996 | Navia et al. .................. 536/4.1 |

OTHER PUBLICATIONS

GB Examination Report issued Aug. 26, 2009 in counterpart application No. GB0803651.9, three (3) pages.
GB Examination Report issued Jun. 3, 2010 in counterpart application No. GB0803651.9, three (3) pages.

* cited by examiner

*Primary Examiner* — Layla Bland
(74) *Attorney, Agent, or Firm* — The Nath Law Group; Tanya E. Harkins

(57) ABSTRACT

A process of azeotropic removal of dimethylformamide, abbreviated as DMF, from a process stream containing DMF requiring its removal, is described wherein the said Process Stream being obtained in a process for preparation of 4,1',6' trichlorogalactosucrose, abbreviated as TGS, or TGS-6-ester including TGS-6-acetate or TGS-6-benzoate, comprising steps of (a) evaporation of the said process stream under reduced pressure to a concentrate to effect removal of a part of DMF azeotropically, (b) diluting the concentrate obtained at the end of step (a.) of this claim with water, preferably to about 5 to 10 times the volume of the said concentrate, and (c) repeating the cycles of evaporation under reduced pressure and dilution with water for more number of times until content of DMF in the concentrated mass is reduced to 0.5% or less of the concentrate.

11 Claims, No Drawings

PROCESS FOR PURIFICATION OF TRICHLOROGALACTOSUCROSE BASED ON DIRECT EXTRACTION IN ORGANIC SOLVENT FROM REACTION MIXTURE FOLLOWED BY EVAPORATIVE REMOVAL OF SOLVENT

TECHNICAL FIELD

The present invention relates to a novel process and a novel strategy for purification of product by direct extraction from the reaction mixture following evaporative solvent removal. followed by direct extraction from the reaction mixture in process for production of chlorinated compounds including sucrose, 1-6-Dichloro-1-6-DIDEOXY-β-Fructofuranasyl-4-chloro-4-deoxy-galactopyranoside.

BACKGROUND OF INVENTION

Strategies of prior art methods of production of 4,1',6' trichlorogalactosucrose (TGS) predominantly involve chlorination of sucrose-6-ester by use of Vilsmeier-Haack reagent derived from various chlorinating agents such as phosphorus oxychloride, oxalyl chloride, phosphorus pentachloride etc, and a tertiary amide such as dimethyl formamide (DMF) leading to preparation of TGS-6-ester. After the said chlorination reaction, the reaction mass is neutralized to pH 7.0-7.5 using appropriate alkali hydroxides of calcium, sodium, etc. to deacetylate the TGS-6-acetate to form 4,1',6' trichlorogalactosucrose.

Conventionally, the purification methods describe firstly the removal of the tertiary amide, usually dimethylformamide (DMF) from the chlorination reaction mixture before proceeding for extractive purification of the desired TGS. Removal of the DMF, from chlorination reaction mixture has been achieved so far by steam stripping (Navia et al 5530106, 5498709) and by drying the entire Process Stream by a method of drying under mild conditions including drying by Agitated Thin Film Dryer, spray drying and the like. There was, however, a need of a more efficient process than the above ones more suitable for industrial production.

SUMMARY OF THE INVENTION

In the present invention, the chlorinated reaction mass prepared from the reaction of sucrose-6-acetate with a Vilsmeier reagent formed from a chlorinating reagent such as phosphorus oxy-chloride, phosphorous penta chloride, triphosgene etc., after neutralization, is directly extracted into water immiscible or sparingly miscible solvent or such solvent mixtures such as ethyl acetate, methyl ethyl ketone, butyl acetate, etc. This extraction is carried out in a suitable liquid-liquid extraction system wherein the chlorinated sucrose derivatives are extracted into the organic layer. Complete extraction of the TGS-6-acetate is monitored. The ratio of aqueous to organic layer ranges from 1:0.8 to 1:8 times depending upon the solvent used for extraction. Packed liquid-liquid extraction columns enables better extraction with reduced solvent consumption.

Significant quantities of DMF get dissolved in the extraction solvent, which prevents use of extractive processes for purification. In this invention, it has been found that it is convenient to remove DMF that gets extracted with TGS-6-acetate azeotropically by repeated dilutions and evaporations under reduced pressure under short path distillation systems such as the Rising Film Evaporators, Falling Film Evaporators, Forced Circulation Evaporators, Agitated Thin Film Evaporators, etc., where the product doesn't get heated to elevated temperatures and solvent removal takes place very efficiently. This approach was never anticipated earlier in process of production of TGS and has succeeded with production system for TGS in this invention.

DETAILED DESCRIPTION OF THE INVENTION

The direct extraction of neutralized chlorinated mass allows the removal of inorganic salts at the very first step. However, during the extraction of the said TGS-6-acetate, varying amount of DMF also partitions into the organic layer, which needs to be removed substantially to prevent its interference in further steps of process of production of TGS, including crystallization.

In an another embodiment, i.e. where deacetylation is carried out, the extraction of the chlorinated reaction mass can also be carried out the same way which shall lead to extraction of TGS as the product in the extraction solvents. However, preferred method is to extract before deacetylation because the partitioning of the TGS-6-acetate in the organic layer is far better. Alternatively the consumption of organic solvent can be minimized, to improve the efficiency of the extraction process, by concentrating the neutralized mass partially or completely and then can be subjected to solvent extraction. The method of concentration can be by the method of molecular separation using a suitable process such as reverse osmosis, etc.

The organic solvent extract containing the TGS-6-acetate or the TGS (in the case of deacetylated neutralized mass) along with other chlorinated sucrose derivatives is then concentrated to evaporate off the organic solvent. This solvent distillation is carried out in short path distillation systems such as the Rising Film Evaporators, Falling Film Evaporators, Forced circulation evaporators, Agitated Thin Film Evaporators, etc., where the product doesn't get heated to elevated temperatures and solvent removal takes place very efficiently. Rotary Vacuum Film Evaporator also results in an evaporation under reduced pressure. However, It is useful only on a laboratory scale, is not useful on an industrial scale and is expressly disclaimed here.

The short path distillation equipments such as Rising Film Evaporators, Falling Film evaporators, Forced circulation evaporators, the Agitated Thin Film Evaporators or the like are designed in such a way that the exposure of the thermally unstable compounds to high temperature is avoided and within a very short period of exposure, the distillation is carried out in a flash. The system operates at high vacuum and low temperatures and low exposure time to the feed for the system.

Rising Film Evaporator: The Feed enters the bottom of the heating tubes and as it heats, vapors begins to form. The ascending force of this vapors produced during the boiling causes liquid and vapors to flow upwards in parallel flow. At the same time the production of vapor increases and the product is pressed as a thin film on the walls of the tubes, and the liquid rises upwards. This co-current upward movement has the beneficial effect of creating a high degree of turbulence in the liquid. This type of evaporator is used with product recirculation, where some of the formed concentrate is reintroduced back to the feed inlet in order to produce sufficient liquid loading inside the boiling tubes.

Falling Film Evaporator: In falling film evaporators, liquid and vapors flow downwards in parallel flow. The liquid to be concentrated is preheated to boiling temperature. An even thin film enters the heating tubes via a distribution device in the head of the evaporator, flows downward at boiling temperature, and is partially evaporated. This gravity-induced downward movement is increasingly augmented by the co-current vapor flow.

Falling film evaporators can be operated with very low temperature differences between the heating media and the boiling liquid, and they also have very short product contact times, typically just a few seconds per pass. These characteristics make the falling film evaporator particularly suitable for heat-sensitive products, and it is today the most frequently used type of evaporator Forced Circulation Evaporator: The circulating liquid is heated when it flows through the heat exchanger and then partially evaporated when the pressure is reduced in the separator, cooling the liquid to the boiling temperature corresponding to this pressure.

The liquid is typically heated only a few degrees for each pass through the heat exchanger, which means the recirculation flow rate has to be high.

After the removal of the extraction solvent from the said extract, the concentrate containing TGS-6-acetate or TGS along with other chlorinated sucrose derivatives with the tertiary amide is mixed with 1:5 to 1:10 times with water and again passed through the said evaporator. The concentrate from the evaporator is diluted with water and again re-evaporated. With every cycle of dilution/reconstitution with water of the said concentrate and re-evaporation, a portion of the tertiary amide present in the concentrate along with water gets removed through every distillation cycle. The number of cycles of concentration and reconstitution varies from 8-20 times depending on several factors including the evaporation conditions and the quantity of the tertiary amide to be removed. Usually, the content of DMF of the concentrate of the initial Process Composition is around 40%, which, in one round of distillation under reduced pressure followed by dilution and about 7 cycles of dilution by addition of water and concentration by distillation under reduced pressure, comes down to about 0.5%, which is low enough to facilitate efficient crystallization or a further process step. The concentrate, containing TGS-6-acetate, after the complete removal or up to a negligible amount of the tertiary amide is taken for deacetylation. The deacetylation is carried out by the addition of appropriate amounts of alkali hydroxides such as calcium hydroxide, sodium hydroxide, etc. The deacetylation was monitored by Thin Layer Chromatography (TLC).

Further isolation of TGS was carried out by any of the following purification methods:
a) Column chromatography
b) Extractive purification The column chromatography could be carried out on an hydrophobic adsorbent like hydrophobic silica gel or it could be done on an appropriate resin packed in a single column or a series of columns having same resin or different type of resins which have an affinity for either the 6-acetyl trichlorogalactosucrose or trichlorogalactosucrose. In the affinity chromatography technique the desired product is adsorbed on the adsorbent matrix and all the solvent and the impurities elute out, The desired product is then eluted out of the column by use of an appropriate The isolated TGS was then crystallized by conventional methods.

The examples given below are only illustrations of preferred embodiment of this invention. They shall in no way be considered to lessen the scope of the invention with respect to actual chemicals used, actual reaction conditions used and the like. This specification covers, at least, every process of production of TGS-6-acetate or TGS wherein DMF is a component of the Process Composition/Reaction Mixture and is required to be removed for making next process step possible. Any adaptation or modification of the embodiments described here or new embodiments that are within the scope of the claims which are obvious to a person skilled in the art are considered as within the scope of this specification. Similarly, any mention of singular is also meant to cover its pleural also unless the context does not permit so. If the said singular refers a generic word, it also encompasses all the specific examples of that kind, unless the context does not permit so. Thus, "a solvent" covers use of all known solvents, of one or more of them, either singly, or in combination as a mixture or as used successively.

Example 1

Removal of Tertiary Amide from Neutralized Chlorinated Mass 80 kg of sucrose-6-acetate was chlorinated by the Vilsmeier reagent generated by $PCl_5$ 252.8 kg) and DMF (480 kg). The chlorination was carried out at elevated temperatures, maintaining 60 minutes at 85° C., 4 hours at 100° C. and at 115° C. for 90 minutes. After chlorination, the reaction mass was neutralized in water and calcium hydroxide slurry was used for adjusting the pH to 6.8. The total volume after neutralization was 3500 L.

The neutralized mass was filtered through the filter press to remove extraneous solids in the solution. Then the solution was subjected to Packed column Liquid-Liquid extraction using 1:3.5 times of ethyl acetate. The layers were separated and the respective layers were analyzed for—TGS-6-acetate content by HPLC and DMF content by GC. It was found that 93% of the TGS-6-acetate was extracted into the organic layer and DMF content was found to be 1.87% of the organic layer extract.

The organic layer was concentrated in RFE (Rising Film Evaporator) to 350 L at 5-7 torr vacuum and 60-65° C. temperature. The DMF content in the concentrate was found to be 33%. The concentrate was diluted to 1800 L with water and then subjected to RFE again and the concentrate obtained was 180 L. The temperature conditions in the RFE was raised to 70-75° C. at 3-5 torr vacuum. The DMF content in the concentrate was found to be 40%. Then the concentrate was diluted to 1000 L using water and again subjected to RFE under similar conditions as the previous concentration. The concentrate obtained was 175 L and the DMF content was 27.6%. Again the concentrate was diluted to 1000 L with water and subjected to RFE at 5 torr vacuum and temperature of 70 75° C. The concentrate obtained was 150 L and DMF content was 12%. Again the dilution was done up to 1000 L and subjected to RFE and concentrate quantity and DMF content was analyzed to be 170 L and 2% respectively. The dilution and concentration was repeated one more time ($5^{th}$ time) at 5 torr vacuum and temperature of 70-75° C. and the DMF content was less than 0.5% in the aqueous concentrate. The TGS-6-acetate loss after the 5 fold dilution and concentration was estimated to be 5-7%. The deacetylation of the TGS-6-acetate was carried out by adding calcium hydroxide up to pH 9.0-9.5 and stirred for 6 hours. TLC was carried out to monitor the deacetylation. After completion of deacylation, the mass was taken for further purification and isolation.

Example 2

Removal of tertiary amide from deacetylated chlorinated mass 80 kg of sucrose-6-acetate was chlorinated by the Vilsmeier reagent generated by $PCl_5$ (252.8 kg) and DMF (480 kg). The chlorination was carried out at elevated temperatures, maintaining 60 minutes at 85° C., 4 hours at 100° C. and at 115° C. for 90 minutes. After chlorination, the reaction mass was neutralized using 30% sodium hydroxide solution and then the pH was further increased up to 9.0 and was stirred for 4-5 hours. The deacetylation was monitored by TLC and after the completion the mass was filtered through the filter press to remove extraneous solids in the solution. The total volume of the filtered solution was found to be 3200 L. Then the solution was subjected to Packed column Liquid-Liquid extraction using 1:4 times of ethyl acetate.

The organic layer was concentrated in ATFD (Agitated Thin Film Dryer) to 500 L at 5-7 torr vacuum and 60-65° C. temperature. The DMF content in the concentrate was found to be 38%. The concentrate was diluted and concentrated in the ATFD number of times and the DMF content reduction is as follows:
a) Dilution with 2000 L water & concentrated to 300 L. DMF—40%.
b) Dilution with 1000 L water & concentrated to 185 L. DMF—42%
c) Dilution with 600 L water & concentrated to 135 L DMF—37.7%
d) Dilution with 400 L water and concentrated to 115 L DMF—21.0%
e) Dilution with 400 L water and concentrated to 100 L DMF—9.15%
f) Dilution with 400 L water and concentrated to 105 L DMF—3.5%
g) Dilution with 250 L water and concentrated to 100 L DMF—0.5%

The TGS loss after the 7 cycles dilution and concentration, after first concentration cycle, was estimated to be 5%.

Example 3

TGS Isolation by Chromatography on Silanized Silica Gel

The aqueous concentrate syrup obtained from example 1 was loaded on to a Stainless Steel column packed with Silanized hydrophobic silica. The quantity of silanized silica gel taken was 10 times the quantity of the aqueous concentrate taken for separation. The mobile phase used to separate the TGS from other chlorinated sucrose derivatives was aqueous buffer at pH 11.0.

The pure product fractions collected from the column chromatographic process were pooled together and concentrated by reverse osmosis membrane system up to a level of 30% concentration of TGS solution. Then the syrupy solution was extracted into ethyl acetate and was subjected to vacuum concentration and crystallization. The overall product loss from the chlorinated reaction mass to crystallization was found to be 15%.

Example 4

TGS Isolation by Extractive Purification

The concentrate obtained after completion of repeated evaporations to make it free from DMF from example 2 was subjected to partial extraction with 1:0.25 v/v of ethyl acetate and hexane so as to remove the majority of the non-polar impurities.

The aqueous layer was then saturated with sodium chloride and the product (4,1',6'-trichlorogalactosucrose) was extracted into 1:3 times v/v of ethyl acetate. The polar impurities were left behind in the aqueous layer.

The ethyl acetate extract was concentrated under vacuum to thick syrupy mass and the product was crystallized from the syrup by dissolving in 1:3 times of methanol. Then the TGS was precipitated by addition of 1:3 times of ethyl acetate and slow removal of methanol by distillation. The crystallized product was 98.9% pure and the yield obtained was 50% from the chlorination stage.

Example 5

Removal of Tertiary Amide from Concentrated Mass After Neutralization 80 kg of sucrose-6-acetate was chlorinated by the Vilsmeier reagent generated by $PCl_5$ 252.8 kg) and DMF (480 kg). The chlorination was carried out at elevated temperatures, maintaining 60 minutes at 85° C., 4 hours at 100° C. and at 115° C. for 90 minutes. After chlorination, the reaction mass was neutralized in water and calcium hydroxide slurry was used for adjusting the pH to 6.8. The total volume after neutralization was 3800 L. This mass was filtered through a filter press to remove the suspended solids and then taken for concentration.

The neutralized mass was then taken for concentration by Reverse Osmosis membrane. The total membrane area required for reducing the volume from 3800 L to 1600 L was 108 $m^2$. The temperature was maintained below 25° C.

During the concentration, the permeate collected was 2200 L with 15% of DMF in the solution.

The concentrate was then extracted with 1:4 times of ethyl acetate using a liquid-liquid extraction column and the organic layer was separated out.

The organic layer was concentrated in ATFD (Agitated Thin Film Dryer) to 500 L at 5-7 torr vacuum and 60-65° C. temperature. The DMF content in the concentrate was found to be 38%. The concentrate was diluted and concentrated in the ATFD number of times and the DMF content reduction is as follows:
h) Dilution with 2000 L water & concentrated to 320 L. DMF—40%.
i) Dilution with 1000 L water & concentrated to 165 L. DMF—38%
j) Dilution with 600 L water & concentrated to 155 L DMF—34.7%
k) Dilution with 400 L water and concentrated to 135 L DMF—16.0%
l) Dilution with 400 L water and concentrated to 100 L DMF—6.15%
m) Dilution with 400 L water and concentrated to 92 L DMF—2.5%
n) Dilution with 250 L water and concentrated to 80 L DMF—0.5%

The TGS loss after the 7 cycles of dilution and concentration was estimated to be 8%.

The organic layer was then proceeded for TGS isolation as per the method described in Example 4.

The invention claimed is:
1. A process of azeotropic removal of dimethylformamide, abbreviated as DMF, from a process stream containing DMF requiring its removal, the process stream being obtained in a process for preparation of 4,1', 6' trichlorogalactosucrose, abbreviated as TGS, or TGS-6-ester, comprising steps of:
   a. evaporating the process stream under reduced pressure to a concentrate to effect removal of a part of DMF azeo- tropically, this step being avoided if the process stream is already at a concentrate stage,
b. diluting the concentrate of step (a.) with water, and repeating the evaporation followed by dilution and evaporation cycles under reduced pressure until DMF concentration reaches low enough to ensure efficient crystallization, and
c. optionally submitting the concentrate of step (b.) for a further purification and isolation of TGS or TGS-6-ester.

2. The process of claim 1 wherein:
a. the TGS ester is TGS acetate or TGS benzoate,
b. the dilution with water is to about 5 to 10 times the volume of the concentrate, and
c. the evaporation is achieved by using distillation in an evaporator under reduced pressure and under a temperature of 55 to 95° C.

3. The process of claim 1, wherein the repeating of the evaporation in step (b.) is done by diluting the concentrate of step (b.) to about 50 percent volume, concentrating the same in RFE to 15 percent of its original volume at 2 to 7 torr vacuum and 70-75° C. to arrive at a concentrate, and continuing to repeat the dilution and concentration under reduced pressure until DMF concentration is 0.5% or less in the concentrate.

4. The process of claim 1 wherein the process stream is result of a process comprising of following steps:
a. preparing a Vilsmeier Reagent selected from (i) [HClC=NR$_2$]$^+$Cl$^-$ where R represents an alkyl group, by reacting a tertiary amide, with an acid chloride or [Bis(trichloromethyl)carbonate] (C$_3$O$_3$Cl$_6$) and (ii) [HPOCl$_2$.OC=NR$_2$]$^+$Cl$^-$ where R represents an alkyl group by reacting a tertiary amide with phosphorus oxychloride,
b. adding sucrose-6-acetate solution, made in DMF, to the Vilsmeier reagent,
c. heating and maintaining the product of step (b.) to 85° C.,
d. heating and maintaining the product of step (c.), to 100° C.,
e. heating and maintaining the product of step (d.) 115° C.,
f. cooling the product of step (e.).

5. The process of claim 4 wherein the alkyl group is a methyl or ethyl group, the tertiary amide is DMF, the acid chloride is phosphorus pentachloride, step (c.) is maintained at 85° C. is for 60 minutes, step (d.) is maintained at 100° C. for 5 hours, and step (e.) is maintained at 115° C. for 90 minutes, and step (f.) cooling is done to 60° C.

6. The process of claim 1, wherein the process for purification comprises column chromatography on one or more of an adsorbent and elution from the same of TGS-6-acetate or TGS with an eluent.

7. The process of claim 1, wherein the process for purification comprises a partial purification by solvent extraction of TGS concentrate by a mixture of organic solvents after saturating the aqueous layer with sodium chloride or any other salt and extraction of TGS in to a solvent that shall leave polar impurities behind in the aqueous layer.

8. The process of claim 7 wherein the solvents comprise 1:0.25 volume/volume of ethyl acetate and hexane and the solvent in which TGS is extracted from salt saturated aqueous layer comprises ethyl acetate.

9. The process of claim 8 comprising a ratio of the concentrate:ethyl acetate of around 1:3.

10. The process of claim 2 wherein the evaporator comprises one or more of a rising film evaporator, a falling film evaporator, a forced circulation evaporator, and an agitated thin film evaporator.

11. The process of claim 2 wherein the cycles of dilution and concentration are repeated at least once.

* * * * *